(12) United States Patent
Yang et al.

(10) Patent No.: US 10,345,253 B2
(45) Date of Patent: Jul. 9, 2019

(54) SYSTEM AND METHOD FOR DETERMINING THE THERMAL PROPERTIES OF ROCKS UNDER HIGH PRESSURE CONDITIONS IN DEEP SEA

(71) Applicant: SOUTH CHINA SEA INSTITUTE OF OCEANOLOGY, CHINESE ACADEMY OF SCIENCES, Guangzhou, Guangdong (CN)

(72) Inventors: Xiaoqiu Yang, Guangzhou (CN); Weiren Lin, Kyoto (JP); Xiaobin Shi, Guangzhou (CN); Hehua Xu, Guangzhou (CN); Ziying Xu, Guangzhou (CN)

(73) Assignee: SOUTH CHINA SEA INSTITUTE OF OCEANOLOGY, CHINESE ACADEMY OF SCIENCES, Guangzhou (CN)

( * ) Notice: Subject to any disclaimer, the term of this patent is extended or adjusted under 35 U.S.C. 154(b) by 140 days.

(21) Appl. No.: 15/556,024

(22) PCT Filed: Apr. 19, 2016

(86) PCT No.: PCT/CN2016/079686
§ 371 (c)(1),
(2) Date: Sep. 6, 2017

(87) PCT Pub. No.: WO2017/152472
PCT Pub. Date: Sep. 14, 2017

(65) Prior Publication Data
US 2018/0113087 A1 Apr. 26, 2018

(30) Foreign Application Priority Data
Mar. 8, 2016 (CN) .......................... 2016 1 0130630

(51) Int. Cl.
*G01K 13/00* (2006.01)
*G01K 1/00* (2006.01)
(Continued)

(52) U.S. Cl.
CPC ................ *G01N 25/20* (2013.01); *G01N 3/12* (2013.01); *G01N 33/24* (2013.01)

(58) Field of Classification Search
USPC .......................... 374/136, 143, 208, 43, 166
See application file for complete search history.

(56) References Cited

U.S. PATENT DOCUMENTS 7,296,927 B2 * 11/2007 Reddy .................... G01N 11/08
374/47
10,215,723 B2 * 2/2019 Yang ........................ G01N 3/08
(Continued)

FOREIGN PATENT DOCUMENTS

CN 101696949 A 4/2010
CN 101949803 A 1/2011
(Continued)

OTHER PUBLICATIONS

International Search Report dated Nov. 25, 2016, issued in counterpart application No. PCT/CN2016/079686, w/ English translation. (8 pages).

*Primary Examiner* — Mirellys Jagan
(74) *Attorney, Agent, or Firm* — Westerman, Hattori, Daniels & Adrian, LLP (57) ABSTRACT

A system for determining the thermal properties of rocks under high pressure conditions in deep sea includes a first pressure vessel having a data collecting unit and a second pressure vessel having a chamber being filled with seawater, communicating with a drain valve, and having a rock sample disposed therein. First and second temperature sensors are respectively disposed in the center and on the surface of the
(Continued)

rock sample. A third temperature sensor and a pressure sensor are disposed in the chamber. Outputs of the temperature sensors and the pressure sensor are communicated with inputs of the data collecting unit via watertight cables. Determining the thermal properties of rocks under high pressure conditions in deep sea includes rapidly opening the drain valve for instant loading of the rock sample and introducing an established finite element numerical inversion model. No heat source for electrical heating nor booster pump is needed.

9 Claims, 4 Drawing Sheets

(51) Int. Cl.
*G01N 25/00* (2006.01)
*G01N 25/20* (2006.01)
*G01N 3/12* (2006.01)
*G01N 33/24* (2006.01)

(56) References Cited

U.S. PATENT DOCUMENTS

| | | | |
|---|---|---|---|
| 2005/0152432 A1* | 7/2005 | Hakimuddin | G01N 3/00 374/53 |
| 2011/0094295 A1* | 4/2011 | Meadows | G01N 3/08 73/38 |
| 2013/0002258 A1* | 1/2013 | Ligneul | E21B 47/06 324/376 |
| 2015/0362419 A1* | 12/2015 | Chertov | G01N 15/088 73/38 |
| 2018/0038812 A1* | 2/2018 | Yang | G01N 3/08 |
| 2018/0120476 A1* | 5/2018 | Yang | G01N 25/20 |

FOREIGN PATENT DOCUMENTS

| | | | |
|---|---|---|---|
| CN | 102053253 A | | 5/2011 |
| CN | 102998332 A | | 3/2013 |
| CN | 105067450 A | | 11/2015 |
| JP | 04050636 A | * | 2/1992 |
| JP | 8-247978 A | | 9/1996 |

\* cited by examiner

SYSTEM AND METHOD FOR DETERMINING THE THERMAL PROPERTIES OF ROCKS UNDER HIGH PRESSURE CONDITIONS IN DEEP SEA

TECHNICAL FIELD

The present invention relates to a system and a method for determining the thermal properties of rocks under high pressure conditions in deep sea, and belongs to the technical field of determination of thermal properties of rocks.

BACKGROUND OF THE INVENTION

The thermal properties of stratum in the earth's interior are the most basic physical parameters, in the study of the thermal structure and thermal evolution in the earth's interior, and the geodynamics. The thermal properties vary under different temperatures and pressures. As such, it is of great significance to study the determination of the thermal properties of rocks under different confining pressures.

At present, the existing methods and systems for determining the thermal properties of rocks under high pressure conditions, usually involve assembling a detector (including a heat source and a temperature sensor) and the rock sample together before setting them in a pressure vessel. The confining pressure in the pressure vessel is then increased to a predetermined value by a booster pump and maintained for a period. When the temperature of the whole system reaches equilibrium, the determination system is turned on so as to perform electrical heating and monitor the change in internal temperature of the rock, and thereby the determination of thermal properties under different confining pressures is achieved.

In the methods and systems mentioned above, active electrical heating (for example, by passing a constant current through a heating wire) is required to serve as a "heat source" for the determination of thermal properties by a transient method. As such, the heat source and the temperature sensor must be both mounted inside the rock. It makes the system complicated. Moreover, the determination of thermal properties has an extreme high requirement on the constancy of temperature, but it is difficult to perform the determination under a constant temperature condition in laboratory since the system is usually exposed to the air. As it is difficult to control the ambient temperature fluctuation, results of the determination are affected greatly most of the time.

In this kind of method and system, active electrical heating (for example, by passing a constant current through a heating wire) is required to serve as the "heat source" for the determination of thermal properties by a transient method.

Our experiments show that, the adiabatic stress derivatives of the temperature ($\Delta T/\Delta \sigma$) of common crustal rocks are usually low (of only 2-6 mK/MPa), while those of pressure mediums (for example, seawater) can reach 17.67 mK/MPa, an order of magnitude higher than that of the common crustal rocks. Therefore, after an instant increase of confining pressure, there will be a temperature difference between the rock sample and the seawater as pressure medium. As such, the present invention has achieved the determination of thermal properties (thermal conductivity, thermal diffusivity, and volumetric heat capacity) under high pressure conditions, by real-time monitoring the temperature changes of the rock sample (in the center and on the surface) and the seawater as pressure medium during the instant increase of confining pressure in the pressure vessel, and employing a finite element numerical inversion method.

SUMMARY OF THE INVENTION

In view of the defects of the prior arts, one objective of the present invention is to provide a system for determining the thermal properties of rocks under high pressure conditions in deep sea, which requires neither a "heat source" for electrical heating nor a booster pump, but has two temperature sensors disposed in the center and on the surface of the rock sample, respectively. By rapidly opening the drain valve to achieve a instant loading for the rock sample, monitoring the temperature changes of the rock sample (in the center and on the surface) and the seawater as the pressure medium during the instant increase of the confining pressure, and introducing an established finite element numerical inversion model in combination with a global optimization method, the thermal properties of the rock sample can be obtained under high pressure conditions. As such, a transient determination of thermal properties, which does not require a "heat source" for electrical heating, is achieved, and thereby the system for determining the thermal properties of rocks under high pressure conditions and the operation thereof are greatly simplified. Meanwhile, within a time scale of 1-3 hours, deep sea water has very little fluctuation in temperature, which makes it an ideal constant temperature environment for determining the thermal properties of rocks. As such, one can obtain more qualitative results of thermal properties determination, which are usually difficult to obtain under laboratory conditions.

In order to achieve the above objective, the present invention provides the following technical solution:

A system for determining the thermal properties of rocks under high pressure conditions in deep sea, said system comprising two pressure vessels, wherein, a data collecting unit is disposed in the first pressure vessel, a chamber filled with pressure medium is formed in the second pressure vessel, and a rock sample is disposed in the chamber; a first temperature sensor is disposed in a center of the rock sample, a second temperature sensor is disposed on a surface of the rock sample, and a third temperature sensor and a pressure sensor are disposed in the chamber; outputs of the first temperature sensor, the second temperature sensor, the third temperature sensor and the pressure sensor are communicated with inputs of the data collecting unit via watertight cables; a drain valve communicated with the chamber is provided on the second pressure vessel.

The surface of the rock sample is provided with a rubber jacket that is configured to watertightly encapsulate the rock sample. A top end and a bottom end of the rock sample are sealed with hard silicone rubber.

The rock sample is of a cylindrical shape.

The pressure medium is seawater.

Another objective of the present invention is to provide a method for determining the thermal properties of rocks under high pressure conditions in deep sea, which requires neither a "heat source" for electrical heating nor a booster pump, but has two temperature sensors disposed respectively in the center and on the surface of the rock sample, respectively. By rapidly opening the drain valve to achieve a instant loading for the rock sample, monitoring the temperature changes of the rock sample (in the center and on the surface) and the seawater as the pressure medium during the instant increase of the confining pressure, and introducing an established finite element numerical inversion model in combination with a global optimization method, the thermal properties of the rock sample can be obtained under high pressure conditions. As such, a transient determination of thermal properties, which does not require a "heat source" for electrical heating, is achieved, and thereby the system for determining the thermal properties of rocks under high pressure conditions and the operation thereof are greatly simplified. Meanwhile, within a time scale of 1-3 hours, deep sea water has very little fluctuation in temperature, which makes it an ideal constant temperature environment for determining the thermal properties of rocks. As such, one can obtain more qualitative results of thermal properties determination, which are usually difficult to obtain under laboratory conditions.

In order to achieve the above objective, the present invention provides the following technical solution:

A method for determining the thermal properties of rocks under high pressure conditions in deep sea, said method comprising the following steps:

step 1: disposing a first temperature sensor in a center of a rock sample having a cylindrical shape, disposing a second temperature sensor on a surface of the rock sample, watertightly encapsulating the rock sample with a rubber jacket, and sealing a top end and a bottom end of the rock sample with hard silicone rubber, so as to obtain a rock sample assembly;

step 2: disposing the rock sample assembly and a third temperature sensor in a second pressure vessel, filling the second pressure vessel with pressure medium, and then sealing the second pressure vessel; connecting the first temperature sensor, the second temperature sensor, the third temperature sensor and a pressure sensor to a data collecting unit with watertight cables, so as to form a system for determining the thermal properties of rocks; turning on a temperature and pressure collecting module of the data collecting unit so as to monitor temperature and confining pressure;

step 3: instant loading: delivering the whole system to a predetermined depth in deep sea by an underwater vehicle; when temperature of the whole system reaches equilibrium, rapidly opening a drain valve by a mechanical arm of the underwater vehicle or an underwater motor so that the confining pressure in the second pressure vessel rises instantaneously to the seawater pressure in deep sea;

step 4: based on changes in the temperature and the confining pressure which are real-time monitored by the data collecting unit, establishing a finite element model and calculating the thermal properties of the rock sample under any confining pressure by inversion.

The step 4 comprises the following steps:

step 41: establishing a finite element numerical model based on a differential equation of heat conduction, in a cylindrical coordinate system which is formed from the center of the rock sample along radial and axial directions of the rock sample;

step 42: let thermal conductivity and volumetric heat capacity of the rock sample be $\lambda$ and $(\rho c)$, respectively, while thermal conductivity and volumetric heat capacity of common crustal rocks are 0.5~6.0 $W \cdot m^{-1} \cdot K^{-1}$ and $0.5 \times 10^6$~$5.0 \times 10^6$ $J \cdot m^{-3} \cdot K^{-1}$ respectively, for a region of $$\begin{cases} \lambda \in [0.5 \ W \cdot m^{-1} \cdot K^{-1}, 6.0 \ W \cdot m^{-1} \cdot K^{-1}] \\ (\rho c) \in [0.5 \times 10^6 \ J \cdot m^{-3} \cdot K^{-1}, 5.0 \times 10^6 \ J \cdot m^{-3} \cdot K^{-1}] \end{cases} \quad (1)$$

dividing $\lambda$ and $(\rho c)$ into m equal portions, so as to obtain $(m+1) \times (m+1)$ initial mesh nodes $(\lambda_i, (\rho c)_j)$, for i, j=1, 2, 3, ..., m;

step 43: inputting each mesh nodes $(\lambda_i, (\rho c)_j)$ into the finite element numerical model, boundary conditions being defined as change of temperature on the surface of the rock sample, T02(t), and change of temperature of the pressure medium, T03(t), which are real-time monitored during the instant loading, and then conducting a simulation to calculate a change of temperature in the center of the rock sample when $(\lambda, (\rho c))=(\lambda_i, (\rho c)_j)$, which is denoted by $T_{i,j}^{mod}$;

step 44, by employing the least squares method, performing a linear fitting of $T_{i,j}^{mod}$ to a change of temperature in the center of the rock sample T01(t):

$$T01(t_k) = K_{i,j} \cdot T_{i,j}^{mod}(t_k) \quad (2)$$

and calculating the slope $K_{i,j}$ and the correlation coefficient $R_{i,j}$ of the fitting line, the correlation coefficient being expressed as $$R_{i,j} = \frac{n \sum_{k=1}^{n} (T_{i,j}^{mod}(t_k) \cdot T01(t_k)) - \left(\sum_{k=1}^{n} T_{i,j}^{mod}(t_k)\right) \cdot \left(\sum_{k=1}^{n} T01(t_k)\right)}{\sqrt{\left[n \sum_{k=1}^{n} (T_{i,j}^{mod}(t_k))^2 - \left(\sum_{k=1}^{n} T_{i,j}^{mod}(t_k)\right)^2\right] \cdot \left[n \sum_{k=1}^{n} (T01(t_k))^2 - \left(\sum_{k=1}^{n} T01(t_k)\right)^2\right]}} \quad (3)$$

wherein n is a total number of samplings, $t_k$ is time when the k-th sampling is performed, $T01(t_k)$ is a change of temperature obtained by the first temperature sensor at $t_k$ after the instant loading, and $1 \leq k \leq n$;

step 45: defining an objective function as $$F(\lambda_i, (\rho c)_j) = 1.0 - (R_{i,j})^2 \quad (4)$$

and calculating objective function value $F(\lambda_i, (\rho c)_j)$ of each mesh node;

step 46: finding a gird node having the smallest objective function value, $F(\lambda_i^0, (\rho c)_j^0) = \min\{F(\lambda_i, (\rho c)_j)\}$, and if $F(\lambda_i^0, (\rho c)_j^0) \leq \varepsilon$ where $\varepsilon$ is a predetermined threshold value for judging whether the requirement for solving the model is met, then $(\lambda_i^0, (\rho c)_j^0)$ is accepted to be a calculated value of the thermal conductivity and volumetric heat capacity of the rock sample, otherwise, for a region being a neighborhood of $(\lambda_i^0, (\rho c)_j^0)$, implementing mesh refinement and returning to the step 43, until $F(\lambda_i^0, (\rho c)_j^0) \leq \varepsilon$ is satisfied, so as to obtained the calculated value of the thermal conductivity and volumetric heat capacity of the rock sample expressed as $(\lambda, (\rho c)) = (\lambda_i^0, (\rho c)_j^0)$;

step 47: calculating a thermal diffusivity of the rock sample by $\kappa = \lambda/(\rho c) = \lambda_i^0/(\rho c)_j^0$.

In the step 41, the differential equation of heat conduction in the cylindrical coordinate system is expressed as $$(\rho c) \frac{\partial T}{\partial t} = \lambda \left( \frac{1}{r} \frac{\partial T}{\partial r} + \frac{\partial^2 T}{\partial r^2} + \frac{\partial^2 T}{\partial z^2} \right) + A \quad (5)$$

$$A = \gamma(\rho c) \frac{\partial P}{\partial t} \quad (6)$$

The initial condition is given as:

$$T(r, z, 0) = 0, (r \leq r_0, |z| \leq z_{02}) \quad (7)$$

The boundary conditions constrained by the change of temperature on the surface of the rock sample, T02(t), and the change of temperature of the pressure medium, T03(t), which are monitored by the system, are given as follow:

$$T(r, z, t) = \begin{cases} T02(t), r = r_0, |z| \le r_0 \\ T03(t), \begin{cases} r = r_0, z_{01} < |z| < z_{02} \\ |z| = z_{02} \end{cases} \end{cases} \quad (8)$$

wherein γ is an adiabatic stress derivative of temperature of various mediums, A is a heat source term driven by change rate of confining pressure ∂P/∂t, $r_0$ is a radius of the rock sample, $z_{01}$ is a vertical distance from a top or bottom of the cylindrical rock sample to a central plane of the rock sample, and $z_{02}$ is a vertical distance from a top or bottom of the encapsulated cylindrical rock sample assembly to the central plane of the rock sample.

The measured change of temperature in the center of the rock sample, T01(t), the change of temperature on the surface of the rock sample, T02(t), and the change of temperature of the pressure medium, T03(t), are defined as the differences between temperatures measured at each time point and temperatures measured at the instant loading:

$T01(t)=T_1(t)-T_1(0)$ $T02(t)=T_2(t)-T_2(0)$ $T03(t)=T_3(t)-T_3(0)$ wherein $T_1(t)$, $T_2(t)$ and $T_3(t)$ are temperatures measured in the step 4 by the first temperature sensor, the second temperature sensor and the third temperature sensor, respectively, at time t after the instant loading; $T_1(0)$, $T_2(0)$ and $T_3(0)$ are temperatures measured in the step 2 by the first temperature sensor, the second temperature sensor and the third temperature sensor, at the instant loading.

Temperature of the whole system for determining the thermal properties of rocks, reaches equilibrium when temperatures measured by the first temperature sensor, the second temperature sensor and the third temperature sensor become steady.

In the method and the system provided by the present invention, the center and the surface of the cylindrical rock sample are respectively provided with a temperature sensor. The rock sample is then encapsulated with a rubber jacket and disposed in a pressure vessel. The system is delivered to a predetermined ocean depth (6,000 meters for example, which has a confining pressure of 60 MPa) by an underwater vehicle. Instant loading (or unloading) for the rock sample is achieved by rapidly opening the drain valves by the underwater vehicle. The system and the method have the following advantages.

1. A "heat source" for electrical heating is not required, while the center and the surface of the cylindrical rock sample are respectively provided with two temperature sensors for monitoring the changes of temperature in the center and on the surface of the rock sample and the change of temperature of seawater as the pressure medium during the instant increase of confining pressure. By establishing a finite element numerical inversion model in combination with the global optimization method, one can obtain the thermal properties of the rock sample under high pressure conditions. As such, a transient determination of thermal properties, which does not require a "heat source" for electrical heating, is achieved, and thereby the system for determining the thermal properties of rocks under high pressure conditions and the operation thereof are greatly simplified.

2. Deep sea, with a very high pressure, is a natural "high pressure pump", and thus the present system can work without stress loading units or pressure pumps.

3. Within a time scale of 1-3 hours, deep sea water has very little fluctuation in temperature, which makes it an ideal constant temperature environment for determining the thermal properties of rocks. As such, one can obtain more qualitative results of thermal properties determination.

Reference characters in the drawings: 1: first pressure vessel; 2: second pressure vessel; 21: drain valve; 22: watertight cables; 3: data collecting unit; 4: rock sample; 41: upper hard silicone rubber; 42: lower hard silicone rubber; 5: rubber jacket; 61: first temperature sensor; 62: second temperature sensor; 63: third temperature sensor; 7: pressure sensor; 8: underwater vehicle; 9: seawater; 10: seafloor.

DETAILED DESCRIPTION OF PREFERRED EMBODIMENT

Further characteristics and advantages of the present invention will be more readily apparent from the below detailed description of the drawings and the embodiment.

Embodiment

Figure 1:
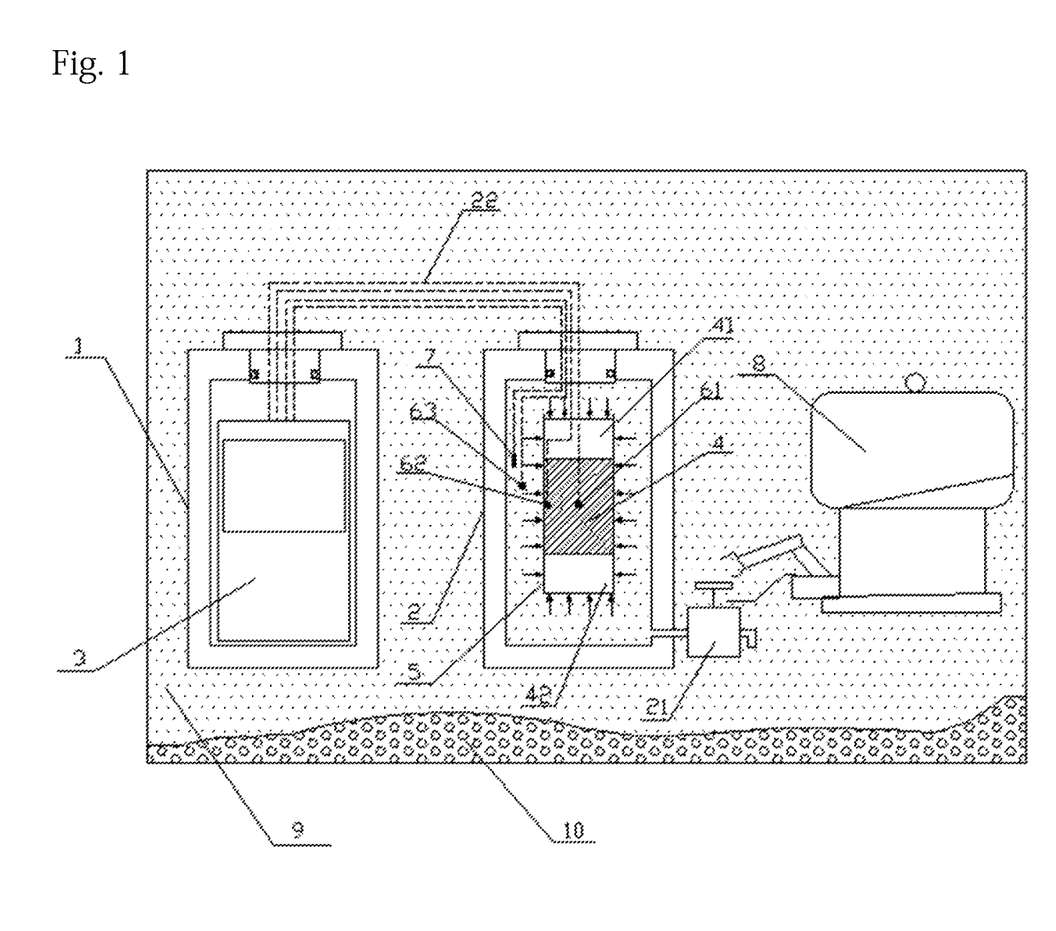
FIG. 1 shows a system of the present invention.

As shown in FIG. 1 is a system for determining the thermal properties of rocks under high pressure condition in deep sea. The system comprises two pressure vessels, a first pressure vessel 1 and a second pressure vessel 2. A data collecting unit 3 is disposed in the first pressure vessel 1, a chamber filled with seawater is formed in the second pressure vessel 2, and a rock sample assembly is disposed in the chamber (the cylindrical rock sample assembly comprises a rock sample 4, a temperature sensor 61 disposed in the center of the sample 4, and a temperature sensor 62 disposed on the surface of the sample 4; a cylindrical upper hard silicone rubber 41 and a cylindrical lower hard silicone rubber 42 are respectively disposed at and pressed tightly against the upper end and the lower end of the cylindrical rock sample 4; then the upper hard silicone rubber 41, the cylindrical rock sample 4, and the lower hard silicone rubber 42 are encapsulated with a rubber jacket 5 for watertight encapsulation and disposed in the chamber of the second pressure vessel 2). Also, a third temperature sensor 63 and a pressure sensor 7 are disposed in the chamber. Outputs of the first temperature sensor 61, the second temperature sensor 62, the third temperature sensor 63 and the pressure sensor 7 are communicated with inputs of the data collecting unit 3 via watertight cables. A drain valve 21 communicated with the chamber is provided on the second pressure vessel 2.

The present invention relates to a method and a system for determining the thermal properties of rocks under high pressure condition in deep sea, and the instant loading for the rock sample 4 is achieved by rapidly opening the drain valve 21 by an underwater vehicle 8. Our experiments showed that, the adiabatic stress derivatives of temperature ($\Delta T/\Delta \sigma$) of common crustal rocks are usually low (of only 2-6 mK/MPa), while those of pressure mediums (for example, silicone oil which is filled in the chamber of the second pressure vessel) can reach 138.74 mK/MPa, two orders of magnitude higher than that of the common crustal rocks. As such, after an instant increase of confining pressure, a temperature difference arises between the rock sample and the pressure medium. And thus one can obtain the thermal properties (thermal conductivity, thermal diffusivity, and volumetric heat capacity) of the rock sample under high pressure, by real-time monitoring the temperature changes of the rock sample (in the center and on the surface) and the seawater as the pressure medium during the instant increase of confining pressure in the pressure vessel, and employing a finite element numerical inversion method.

The finite element numerical model and method for the inversion of thermal properties are as follows.

Step 1: Differential equation of heat conduction

Figure 2:
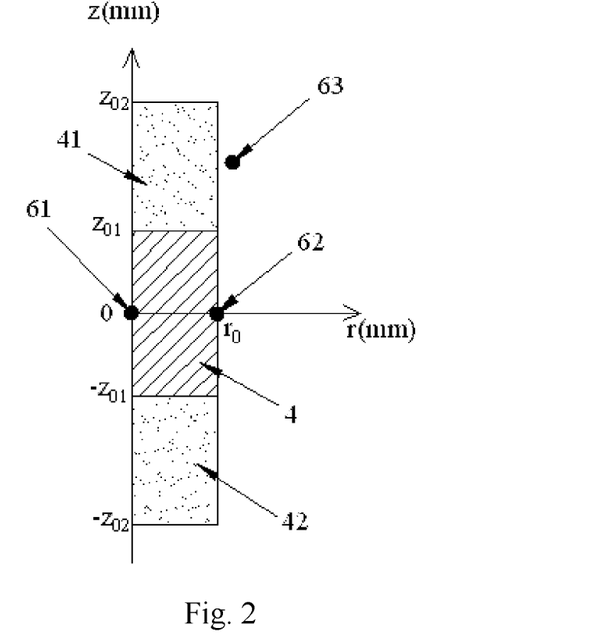
FIG. 2 shows a finite element numerical model in a two-dimensional cylindrical coordinate system.

Since the rock sample is prepared into a cylindrical shape, in order to facilitate the calculation, the first temperature sensor 61 is disposed in the center( ) of the rock sample, and the second temperature sensor 62 is disposed on the rock sample at the same radial plane with the first temperature sensor 61. As such, the differential equation of heat conduction in the corresponding cylindrical coordinate system (2drz) can be expressed as $$\rho c \frac{\partial T}{\partial t} = \lambda \left( \frac{1}{r} \frac{\partial T}{\partial r} + \frac{\partial^2 T}{\partial r^2} + \frac{\partial^2 T}{\partial z^2} \right) + A, \tag{9}$$

$$A = \gamma(\rho c) \frac{\partial P}{\partial t}, \tag{10}$$

The initial condition is given as:

$$T(r,z,0)=0, (r \leq 25 \text{ mm}, |z| \leq 65 \text{ mm}), \tag{11}$$

The boundary conditions constrained by the change of temperature on the surface of the rock sample, T02(t), and the change of temperature of the pressure medium, T03(t), which are monitored by the system, are given as follow:

$$T(r,z,t) = \begin{cases} T02(t), r = 25 \text{ mm}, |z| \leq 25 \text{ mm} \\ T03(t), \begin{cases} r = 25 \text{ mm}, 25 \text{ mm} < |z| < 65 \text{ mm} \\ |z| = 65 \text{ mm} \end{cases} \end{cases} \tag{12}$$

wherein $\lambda$ and $\rho c$ represent the thermal conductivity and the volumetric heat capacity of various mediums respectively, $\gamma$ is an adiabatic stress derivative of temperature of various mediums, A is a heat source term driven by change rate of confining pressure $\partial P/\partial t$.

The finite element numerical model is then established in the cylindrical coordinate system (2drz) according to the above differential equation of heat conduction. as shown in FIG. 2.

Step 2: let thermal conductivity and volumetric heat capacity of the rock sample be $\lambda$ and ($\rho c$) respectively, while thermal conductivity and volumetric heat capacity of common crustal rocks are 0.5~6.0 W·m$^{-1}$·K$^{-1}$ and 0.5×10$^6$~5.0× 10$^6$ J·m$^{-3}$·K$^{-1}$, respectively; in order to broaden the adaptability of the present inversion method, one can appropriately increase the region for solving the thermal properties of rocks $$\begin{cases} \lambda \in [0.5 \text{ W} \cdot m^{-1} \cdot K^{-1}, 6.0 \text{ W} \cdot m^{-1} \cdot K^{-1}] \\ (\rho c) \in [0.5 \times 10^6 \text{ J} \cdot m^{-3} \cdot K^{-1}, 5.0 \times 10^6 \text{ J} \cdot m^{-3} \cdot K^{-1}] \end{cases} \tag{13}$$

and both $\lambda$ and ($\rho c$) are divided into m equal portions, so as to obtain (m+1)×(m+1) initial mesh nodes ($\lambda_i$, ($\rho c$)$_j$), for i, j=1, 2, 3, . . . , m;

Step 3: inputting each mesh nodes ($\lambda_i$, ($\rho c$)$_j$) into the PT-FE finite element numerical model, boundary conditions being defined as change of temperature on the surface of the rock sample, T02(t), and change of temperature of the pressure medium, T03(t), which are real-time monitored during the instant loading, and then conducting a simulation to calculate a change of temperature in the center of the rock sample when ($\lambda$, ($\rho c$))=($\lambda_i$, ($\rho c$)$_j$), which is denoted by $T_{i,j}^{mod}$;

Step 4: by employing the least squares method, performing a linear fitting of $T_{i,j}^{mod}$ to a change of temperature in the center of the rock sample T01(t):

$$T01(t_k)=K_{i,j} \cdot T_{i,j}^{mod}(t_k) \tag{14}$$

and calculating the slope $K_{i,j}$ and the correlation coefficient $R_{i,j}$ of the fitting line, the correlation coefficient being expressed as $$R_{i,j} = \frac{n\sum_{k=1}^{n}(T_{i,j}^{mod}(t_k) \cdot T01(t_k)) - \left(\sum_{k=1}^{n} T_{i,j}^{mod}(t_k)\right) \cdot \left(\sum_{k=1}^{n} T01(t_k)\right)}{\sqrt{\left[n\sum_{k=1}^{n}(T_{i,j}^{mod}(t_k))^2 - \left(\sum_{k=1}^{n} T_{i,j}^{mod}(t_k)\right)^2\right] \cdot \left[n\sum_{k=1}^{n}(T01(t_k))^2 - \left(\sum_{k=1}^{n} T01(t_k)\right)^2\right]}} \tag{15}$$

Step 5: defining an objective function as $$F(\lambda_i,(\rho c)_j)=1.0-(R_{i,j})^2 \tag{16}$$

and calculating objective function value $F(\lambda_i, (\rho c)_j)$ of each mesh node, for i, j=1, 2, 3, . . . , m;

Step 6: finding a gird node having the smallest objective function value, $F(\lambda_i^0, (\rho c)_j^0)=\min\{F(\lambda_i, (\rho c)_j)\}$, and if $F(\lambda_i^0, (\rho c)_j^0) \leq \varepsilon$ where $\varepsilon$ is a predetermined threshold value for judging whether the requirement for solving the model is met, then ($\lambda_i^0$, ($\rho c$)$_j^0$) is accepted to be a calculated value of the thermal conductivity and volumetric heat capacity of the rock sample, otherwise, for a region being a neighborhood of ($\lambda_i^0$, ($\rho c$)$_j^0$), implementing mesh refinement and returning to the step 3, until $F(\lambda_i^0, (\rho c)_j^0) \leq \varepsilon$ is satisfied, so as to obtained the calculated value of the thermal conductivity and volumetric heat capacity of the rock sample, $(\lambda, (\rho c))=(\lambda_i^0, (\rho c)_j^0)$;

Step 7: calculating a thermal diffusivity of the rock sample by $\varkappa=\lambda/(\rho c)=\lambda_i^0/(\rho c)_j^0$. And thereby the calculation of the thermal properties of rock under a certain confining pressure is complete.

In a practical measurement, the whole system is delivered to a predetermined depth (6,000 meters for example, having a pressure of 60 MPa.) in deep sea by an underwater vehicle 8. When temperature of the whole system reaches equilibrium, rapidly opening the drain valve by a mechanical arm of the underwater vehicle, so that the confining pressure in the second vessel 2 rises instantaneously to the seawater pressure (for example, 60 MPa) within 1-2 seconds. Since the adiabatic stress derivatives of temperature of the rock sample and that of the pressure medium (seawater for example) differ by one order of magnitude, a temperature difference arises between the rock sample and the pressure medium. By monitoring the temperature changes of the rock sample (in the center and on the surface) and the seawater as the pressure medium during the instant increase of the confining pressure, and employing an established finite element numerical inversion model in combination with a global optimization method, one can obtain the thermal properties of the rock sample under high pressure conditions. As such, a transient determination of thermal properties, which does not require a "heat source" for electrical heating, is achieved, and thereby the system for determining the thermal properties of rocks under high pressure conditions and the operation thereof are greatly simplified.

The method of the present invention comprises the following steps:

Step 1: disposing the first temperature sensor 61 in the center of the cylindrical rock sample 4, disposing the second temperature sensor 62 on the surface of the rock sample 4, and watertightly encapsulating the rock sample 4 with the rubber jacket 5, so as to obtain a rock sample assembly.

Step 2: disposing the rock sample assembly, the pressure sensor 7 and the third temperature sensor 63 in the second pressure vessel 2, and then sealing the second pressure vessel 2; connecting the outputs of the first temperature sensor 61, the second temperature sensor 62, the third temperature sensor 63 and the pressure sensor 7 to the data collecting unit 3 with watertight cables 22, as shown in FIG. 1; turning on a temperature and pressure collecting module, so as to monitor the temperature and the confining pressure.

Step 3: after assembling of the whole system is complete, delivering the whole system to a predetermined depth of seawater 9 in deep sea (the depth can be 6,000 meters for example, which has a pressure of 60 MPa; the bottom of seawater 9 is denoted by seafloor 10) by an underwater vehicle 8; when temperature of the whole system reaches equilibrium, rapidly opening the drain valve 21 by a mechanical arm of the underwater vehicle so that the confining pressure in the second pressure vessel 2 rises instantaneously to the seawater pressure (for example, 60 MPa) within 1-2 seconds.

The instant loading of the rock sample is achieved by the above operation. During the process, the changes of temperature and confining pressure are real-time monitored and collected. By employing the above finite element numerical model for inversion of thermal properties, the thermal properties of rocks can be obtained under a certain confining pressure.

The inventors had performed a test using a system practically consistent with that of the present invention, but different in that they introduced a high pressure pump to raise the confining pressure in a large pressure vessel (configured to simulate a deep sea environment having high pressure, for example, 130 MPa). As such, the confining pressure in the other pressure vessel which contains the rock sample assembly rose instantaneously once the drain valve was open.

Figure 3:
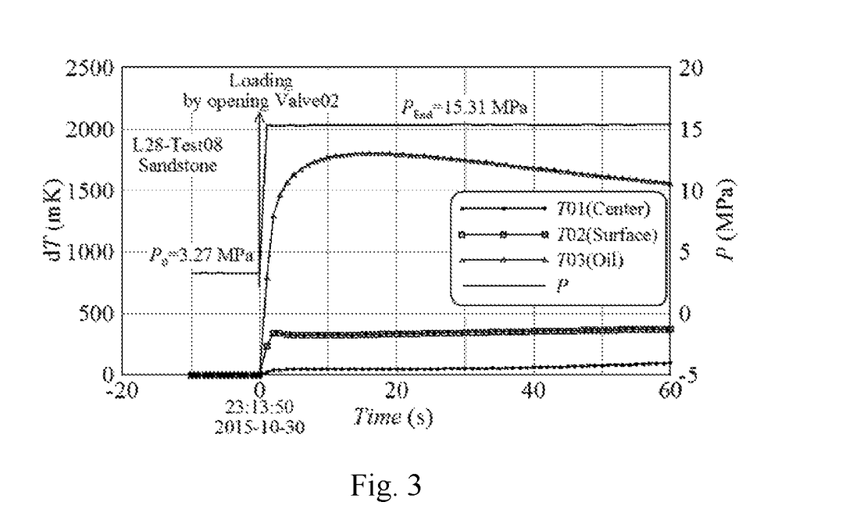
FIG. 3 shows the temperature response curve of a sandstone sample (L28) during an instant loading process. The sample was collected from the Longmenshan Fault Zone, China.
Figure 4:
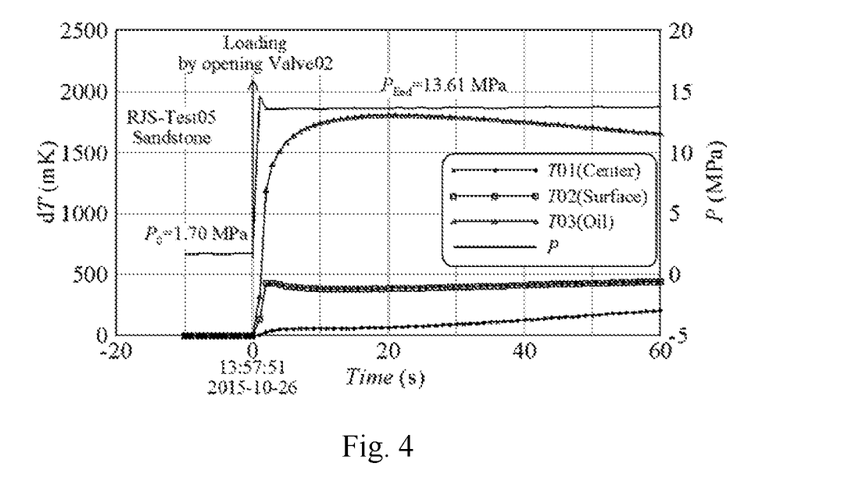
FIG. 4 shows the temperature response curve of a sandstone sample (RJS) during an instant loading process. The sample was collected from Rajasthan, India.

FIGS. 3 and 4 show the temperature response curves during an instant loading process on a sandstone sample (L28) collected from the Longmenshan Fault Zone, China, and a sandstone sample (RJS) collected from Rajasthan, India. Table 1 shows the results of the thermal properties determination under the confining pressures of 15.31 MPa and 13.61 MPa for the sandstone samples L28 and RJS.

TABLE 1

Results of inversion of thermal properties

| Sample ID | $\lambda$ (W·m$^{-1}$·K$^{-1}$) | $(\rho c)$ ($\times 10^6$J/(m$^3$ K)) | $\kappa$ ($\times 10^{-6}$m$^2$·s) | P (MPa) |
|---|---|---|---|---|
| L28 | 1.366 | 1.261 | 1.084 | 15.31 |
| RJS | 3.273 | 1.737 | 1.884 | 13.61 |

Figure 5:
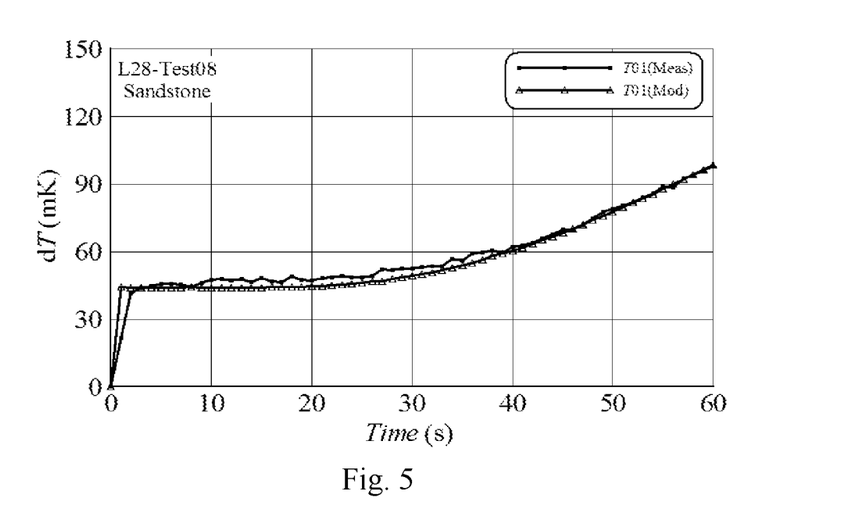
FIG. 5 shows the comparison between the measurement results and the simulation results of a sandstone sample (L28) collected from the Longmenshan Fault Zone, China.
Figure 6:
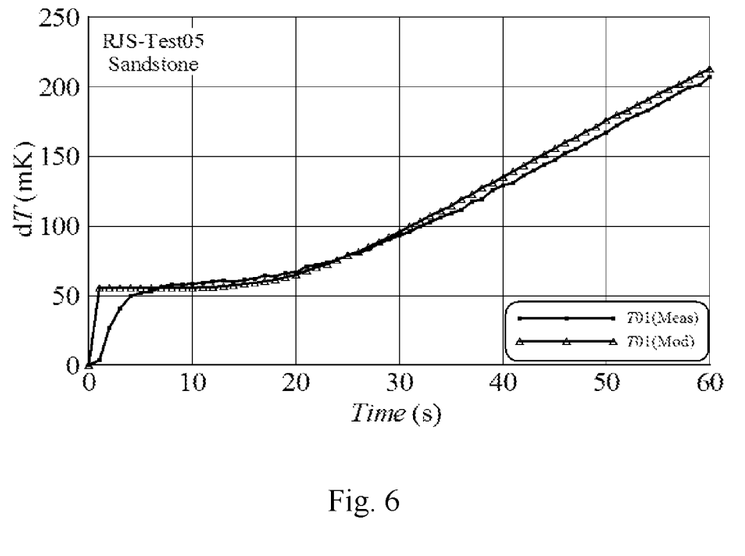
FIG. 6 shows the comparison between the measured temperatures and the simulated temperatures of the center of a sandstone sample (RJS) collected from Rajasthan, India.

Comparisons between the measure results and the simulated results of the sandstone samples L28 and RJS are as shown in FIGS. 5 and 6, respectively. The method and the system provided by the present invention, can not only be used for determining the thermal properties of rocks under high pressure condition in deep sea, but also greatly simplify the existing systems and operation.

The above detailed description is a specific explanation for feasible embodiments of the present invention. The embodiments are not used for limiting the scope of the present invention. Any equivalent or changes made on the basis of the present invention shall fall within the scope of the present invention.

The invention claimed is:

1. A system for determining the thermal properties of rocks under high pressure conditions in deep sea, said system comprising:
    a first pressure vessel having a data collecting unit;
    a second pressure vessel having a chamber filled with a pressure medium and a drain valve communicating with the chamber, the chamber having a rock sample disposed therein;
    a first temperature sensor disposed in a center of the rock sample;
    a second temperature sensor disposed on a surface of the rock sample;
    a third temperature sensor disposed in the chamber; and
    a pressure sensor disposed in the chamber,
    wherein outputs of the first temperature sensor, the second temperature sensor, the third temperature sensor and the pressure sensor are communicated with inputs of the data collecting unit via watertight cables.

2. The system according to claim 1, wherein the surface of the rock sample is provided with a rubber jacket that is configured to watertightly encapsulate the rock sample, and a top end and a bottom end of the rock sample are sealed with hard silicone rubber.

3. The system according to claim 1, wherein the rock sample is of a cylindrical shape.

4. The system according to claim 1, wherein the pressure medium is seawater.

5. A method for determining the thermal properties of rocks under high pressure conditions in deep sea, said method comprising the steps of:

step 1: disposing a first temperature sensor in a center of a rock sample having a cylindrical shape, disposing a second temperature sensor on a surface of the rock sample, watertightly encapsulating the rock sample with a rubber jacket, and sealing a top end and a bottom end of the rock sample with hard silicone rubber, so as to obtain a rock sample assembly;

step 2: disposing the rock sample assembly and a third temperature sensor in a pressure vessel, filling the pressure vessel with a pressure medium, and then sealing the pressure vessel; connecting the first temperature sensor, the second temperature sensor, the third temperature sensor and a pressure sensor to a data collecting unit with watertight cables, so as to form a system for determining the thermal properties of rocks; and turning on a temperature and pressure collecting module of the data collecting unit so as to monitor temperature and confining pressure;

step 3: instant loading: delivering the system to a predetermined depth in deep sea by an underwater vehicle; when a temperature of the system reaches equilibrium, rapidly opening a drain valve by a mechanical arm of the underwater vehicle or an underwater motor so that the confining pressure in the pressure vessel rises to the seawater pressure in deep sea;

step 4: based on changes of the temperature and the confining pressure which are real-time monitored by the data collecting unit, establishing a finite element model and calculating the thermal properties of the rock sample under the confining pressure by inversion.

6. The method according to claim 5, wherein when temperatures measured by the first temperature sensor, the second temperature sensor and the third temperature sensor become steady, a temperature of the system reaches equilibrium.

7. The method according to claim 5, wherein step 4 further comprises the steps of:

step 41: establishing a finite element numerical model based on a differential equation of heat conduction, in a cylindrical coordinate system which is formed from the center of the rock sample along radial and axial directions of the rock sample;

step 42: let a thermal conductivity and volumetric heat capacity of the rock sample be $\lambda$ and $(\rho c)$, respectively, while a thermal conductivity and volumetric heat capacity of common crustal rocks are 0.5~6.0 W·m$^{-1}$·K$^{-1}$ and $0.5\times10^6$~$5.0\times10^6$ J·m$^{-3}$·K$^{-1}$, respectively, for a region of $$\begin{cases} \lambda \in [0.5 \text{ W}\cdot m^{-1}\cdot K^{-1}, 6.0 \text{ W}\cdot m^{-1}\cdot K^{-1}] \\ (\rho c) \in [0.5\times 10^6 \text{ J}\cdot m^{-3}\cdot K^{-1}, 5.0\times 10^6 \text{ J}\cdot m^{-3}\cdot K^{-1}] \end{cases} \quad (1)$$

dividing $\lambda$ and $(\rho c)$ into m equal portions, so as to obtain $(m+1)\times(m+1)$ initial mesh nodes $(\lambda_i, (\rho c)_j)$, for i, j=1, 2, 3, ..., m;

step 43: inputting each mesh nodes $(\lambda_i, (\rho c)_j)$ into the finite element numerical model, boundary conditions being defined as a change of temperature on the surface of the rock sample, T02(t), and a change of temperature of the pressure medium, T03(t), which are real-time monitored during the instant loading, and then conducting a simulation to calculate a change of temperature in the center of the rock sample when $(\lambda, (\rho c))=(\lambda_i, (\rho c)_j)$, which is denoted by $T_{i,j}^{mod}$;

step 44: by employing the least squares method, performing a linear fitting of $T_{i,j}^{mod}$ to a change of temperature in the center of the rock sample T01 (t):

$$T01(t_k) = K_{i,j} \cdot T_{i,j}^{mod}(t_k) \quad (2)$$

and calculating the slope $K_{i,j}$ and the correlation coefficient $R_{i,j}$ of the fitting line, the correlation coefficient being expressed as $$R_{i,j} = \frac{n\sum_{k=1}^{n}(T_{i,j}^{mod}(t_k)\cdot T01(t_k)) - \left(\sum_{k=1}^{n}T_{i,j}^{mod}(t_k)\right)\cdot\left(\sum_{k=1}^{n}T01(t_k)\right)}{\sqrt{\left[n\sum_{k=1}^{n}(T_{i,j}^{mod}(t_k))^2 - \left(\sum_{k=1}^{n}T_{i,j}^{mod}(t_k)\right)^2\right]\cdot\left[n\sum_{k=1}^{n}(T01(t_k))^2 - \left(\sum_{k=1}^{n}T01(t_k)\right)^2\right]}} \quad (3)$$

wherein n is a total number of samplings, $t_k$ is time when the k-th sampling is performed, $T01(t_k)$ is a change of temperature obtained by the first temperature sensor at $t_k$ after the instant loading, and $1\leq k\leq n$;

step 45: defining an objective function as $$F(\lambda_i, (\rho c)_j) = 1.0 - (R_{i,j})^2 \quad (4)$$

and calculating objective function value $F(\lambda_i, (\rho c)_j)$ of each mesh node;

step 46: finding a gird node having the smallest objective function value, $F(\lambda_i^0, (\rho c)_j^0) = \min\{F(\lambda_i, (\rho c)_j)\}$, and if $F(\lambda_i^0, (\rho c)_j^0) \leq \varepsilon$ where $\varepsilon$ is a predetermined threshold value for judging whether the requirement for solving the model is met, then $(\lambda_i^0, (\rho c)_j^0)$ is accepted to be a calculated value of the thermal conductivity and volumetric heat capacity of the rock sample, otherwise, for a region being a neighborhood of $(\lambda_i^0, (\rho c)_j^0)$, implementing mesh refinement and returning to the step 43, until $F(\lambda_i^0, (\rho c)_j^0) \leq \varepsilon$ is satisfied, so as to obtain the calculated value of the thermal conductivity and volumetric heat capacity of the rock sample expressed as $$(\lambda, (\beta c)) = (\lambda_i^0, (\rho c)_j^0);$$

step 47: calculating a thermal diffusivity of the rock sample by $\kappa = \lambda/(\rho c) = \lambda_i^0/(\rho c)_j^0$.

8. The method according to claim 7, wherein, in the step 41, the differential equation of heat conduction in the cylindrical coordinate system is expressed as $$(\rho c)\frac{\partial T}{\partial t} = \lambda\left(\frac{1}{r}\frac{\partial T}{\partial r} + \frac{\partial^2 T}{\partial r^2} + \frac{\partial^2 T}{\partial z^2}\right) + A \quad (5)$$

$$A = \gamma(\rho c)\frac{\partial P}{\partial t} \quad (6)$$

an initial condition is given as:

$$T(r,z,0) = 0, (r \leq r_0, |z| \leq z_{02}) \quad (7)$$

the boundary conditions constrained by the change of temperature on the surface of the rock sample, T02(t), and the change of temperature of the pressure medium, T03(t), which are monitored by the system, are given as follow:

$$T(r, z, t) = \begin{cases} T02(t), r = r_0, |z| \le r_0 \\ T03(t), \begin{cases} r = r_0, z_{01} < |z| < z_{02} \\ |z| = z_{02} \end{cases} \end{cases} \quad (8)$$

wherein γ is an adiabatic stress derivative of temperature of various mediums, A is a heat source term driven by change rate of confining pressure ∂P/∂t, $r_0$ is a radius of the rock sample, $z_{01}$ is a vertical distance from a top or bottom of the cylindrical rock sample to a central plane of the rock sample, and $z_{02}$ is a vertical distance from a top or bottom of the encapsulated cylindrical rock sample assembly to the central plane of the rock sample.

9. The method according to claim 8, wherein the measured change of temperature in the center of the rock sample, T01(t), the change of temperature on the surface of the rock sample, T02(t), and the change of temperature of the pressure medium, T03(t), are defined as the differences between temperatures measured at each time point and temperatures measured at the instant loading:

$$T01(t) = T_1(t) - T_1(0)$$

$$T02(t) = T_2(t) - T_2(0)$$

$$T03(t) = T_3(t) - T_3(0)$$

wherein $T_1(t)$, $T_2(t)$ and $T_3(t)$ are temperatures measured in the step 4 by the first temperature sensor, the second temperature sensor and the third temperature sensor respectively, at time t after the instant loading; $T_1(0)$, $T_2(0)$ and $T_3(0)$ are temperatures measured in the step 2 by the first temperature sensor, the second temperature sensor and the third temperature sensor, at the instant loading.

* * * * *